United States Patent [19]

Wäjen et al.

[11] Patent Number: 4,873,244

[45] Date of Patent: Oct. 10, 1989

[54] TRICYCLIC HETEROCYCLIC COMPOUNDS AS PSYCHOPHARMACEUTICALS

[75] Inventors: Frank Wäjen, Vaerlose; Holger C. Hansen, Ballerup, both of Denmark

[73] Assignee: A/S Ferrosan, Soborg, Denmark

[21] Appl. No.: 156,363

[22] Filed: Feb. 16, 1988

[30] Foreign Application Priority Data

Mar. 18, 1987 [DK] Denmark .............................. 1374/87

[51] Int. Cl.$^4$ .................. A61K 31/505; C07D 471/14; C07D 487/04
[52] U.S. Cl. .................................... 514/250; 514/267; 514/292; 514/293; 544/229; 544/250; 544/251; 544/346; 546/14; 546/82; 546/84
[58] Field of Search .............. 544/250, 251, 346, 229; 546/82, 14, 84; 514/250, 267, 293, 292

[56] References Cited

U.S. PATENT DOCUMENTS

| 4,440,929 | 4/1984 | Lee et al. ............................ 544/346 |
| 4,771,051 | 9/1988 | Wätjen et al. ....................... 514/267 |
| 4,774,245 | 9/1988 | Wätjen et al. ....................... 514/250 |

Primary Examiner—Richard A. Schwartz
Attorney, Agent, or Firm—Gordon W. Hueschen

[57] ABSTRACT

New heterocyclic compounds having the general formula

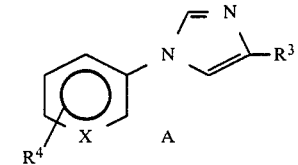

wherein

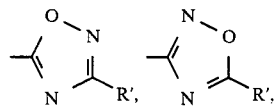

$CO_2R'$ or $CONR'R''$,
wherein
$R'$ and $R''$ independently are $C_{1-6}$-alkyl, $C_{3-7}$-cycloalkyl or $C_{1-6}$-alkoxymethyl;
—A— is —C(=O)—NR'''—, —NR'''—C(=O)—, or

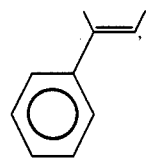

wherein
$R'''$ is $C_{1-6}$-alkyl;
X is C or N; and
$R^4$ is hydrogen, halogen, CN, $C_{1-6}$-alkyl, $C_{1-6}$-alkynyl, trimethylsilyl-$C_{1-6}$-alkynyl, aryloxy which may be substituted with halogen, aralkoxy, $C_{3-7}$-cycloalkoxy which may be substituted with one or more $C_{1-6}$-alkyl groups, or NR''''R''''', wherein R'''' and R''''' independently are $C_{1-6}$-alkoxy or together with the nitrogen atom form a 3-7 membered heterocyclic ring.

The compounds are useful in psychopharmaceutical preparations as anticonvulsants, anxiolytics, hypnotics, and nootropics.

9 Claims, No Drawings

TRICYCLIC HETEROCYCLIC COMPOUNDS AS PSYCHOPHARMACEUTICALS

The present invention relates to therapeutically active heterocyclic compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of heterocyclic compounds have strong affinity for the benzodiazepine receptors which make them useful in psychopharmaceutical preparations.

Accordingly, it is an object of the invention to provide such novel heterocyclic compounds.

The heterocyclic compounds of the invention have the general formula I

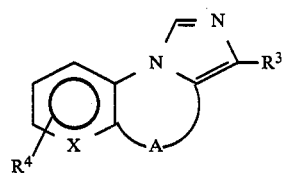
(I)

wherein
$R^3$ is

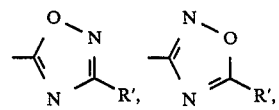

$CO_2R'$ or $CONR'R''$,
wherein
$R'$ and $R''$ independently are $C_{1-6}$-alkyl, $C_{3-7}$-cycloalkyl or $C_{1-6}$-alkoxymethyl;
—A— is —C(=O)—NR'''—, —NR'''—C(=O)—, or

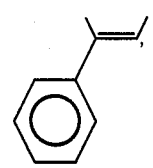

wherein
$R'''$ is $C_{1-6}$-alkyl;
X is C or N; and
$R^4$ is hydrogen, halogen, CN, $C_{1-6}$-alkyl, $C_{1-6}$-alkynyl, trimethyl-$C_{1-6}$-alkynl, aryloxy which may be substituted with halogen, aralkoxy, $C_{3-7}$-cycloalkoxy which may be substituted with one or more $C_{1-6}$-alkyl groups, or $NR''''R'''''$, wherein $R''''$ and $R'''''$ independently are $C_{1-6}$-alkyl or together with the nitrogen atom form a 3-7 membered heterocyclic ring.

The invention also relates to a method of preparing the above mentioned compounds. This method comprises:

(a) reacting a compound of formula II

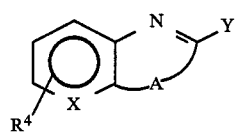
(II)

wherein —A—, X and $R^4$ have the meanings set forth above and wherein Y is a leaving group, with a compound having the formula III $$CN—CH_2—R^3 \quad (III)$$

wherein $R^3$ has the meaning set forth above, to form a compound of the invention, or (b) reacting a reactive deivative of a compound having the general formula IV

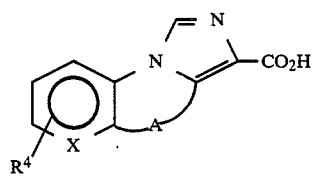
(IV)

wherein —A—, X and $R^4$ have the meanings set forth above with a compound having the general formula V $$R'—C(=NOH)NH_2 \quad (V)$$

wherein $R'$ has the meaning set forth above to form a compound of the general formula I wherein $R^3$ is

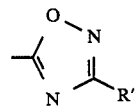

wherein $R'$ has the meaning set forth above, or (c) reacting a compound having the general formula VI

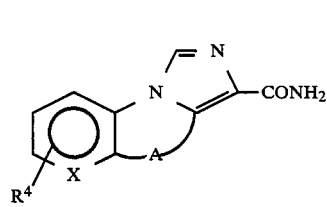
(VI)

wherein —A—, X and $R^4$ have the meanings set forth above, with a compound having the general formula VII $$R'—C(OCH_3)_2N(CH_3)_2 \quad (VII)$$

wherein $R'$ has the meaning set forth above, to form a compound having the general formula VIII

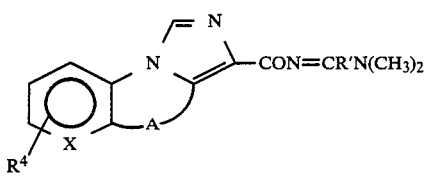

wherein —A—, X and R⁴ have the meanings set forth above and reacting the compound having the formula (VIII) with NH₂OH or another aminating agent, to form a compound having the general formula I, wherein R³ is

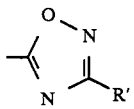

wherein R' has the meaning defined above, or (d) reacting a compound having the general formula IX

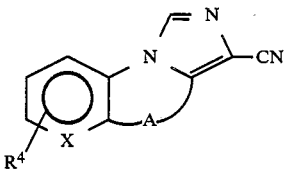

wherein —A—, X, R⁴ have the meanings set forth above, with NH₂OH to form a compound having the general formula X

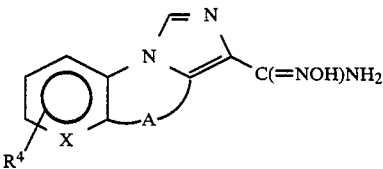

wherein —A—, X, R⁴ the meanings set forth above, and reacting the compound having the formula (X) with R'-COCl or (R'CO)₂O wherein R' has the meaning set forth above, to form a compound of formula I, wherein R³ is

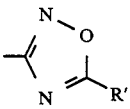

wherein R' has the meaning set forth above, or (e) reacting a compound having the general formula I, wherein —A—, X and R³ have the meanings set forth above and R⁴ is halogen, with cyanide, an alkohol, a phenol or an amine, to form a compound of formula I, wherein R⁴ is cyano, or an aryloxy, aralkoxy, cycloalkoxy or amino group which may all be substituted, or (f) reacting a reactive derivative of a compound having the formula IV, wherein —A—, X and R⁴ have the meanings set forth above with an amine, to form a compound of formula I, wherein R⁴ is CONR'R", wherein R' and R" have the meanings set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)₂ wherein R is lower-alkyl or —OP(O)(NR'R") R' and R" each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (—40) degrees Celsius to about room temperature is accordingly usually particularly suitable.

The starting materials may be prepared from commercially available benzene derivatives and by using well known synthetic methods and as described in Synthesis, Vol. 10, pp. 681–682.

The pharmaceutical properties of the compounds of the invention can be illustrated by determining their capability for displacing radioactive labelled flunitrazepam from benzodiazepine receptors.

The displacement activity of the compounds of the invention may be found by determining the ED₅₀ value. The ED₅₀ value represents the dose (mg/kg) of a test substance which causes the specific binding of flunitrazepam to benzodiazepine receptors in a living brain to be reduced to 50% of the control value.

Such an in vivo test is carried out as follows:

Principle. Twenty minutes after a dose of ³H-flunitrazepam (³H-FNM) (200 μCi/kg, i.v.) the amount of specific ³H-FNM binding to brain benzodiazepine receptors has reached its maximal value. This specific binding of ³H-FNM can be partly or completely prevented by simultaneous or prior administration of pharmacologically active benzodiazepines and by some benzodiazepine-like agents (Chang and Snyder, Eur. J. Pharmacol. 48, 212–218 (1978)).

Test procedure. Suspensions of test substances (2 mg/ml) are prepared in 5% Duphasol-X (TM Duphar, castor oil-ethylene oxide derivative for emulsifying and solubilizing oil and other water-insoluble substances) by sonification for 10 min using a Branson B15 microtip ultrasonifier (setting 7). Groups of three mice (female, NMR, 18–22 grams) are injected with the test substance at 100 mg/kg intraperitoneally. Fifteen minutes after test substance administration the mice are challenged with 4 μCi intravenously of ³H-FNM (70–90 Ci/mole) in 200 μl physiological saline. Twenty minutes after ³H-FNM administration mice are sacrificed by decapitation, the forebrains rapidly excised (within 30 sec) and homogenized in 12 ml of icecold 25 mM KH₂PO₄, pH 7.1, using an Ultra-Turrax homogenizer fitted with an N 10 shaft. Two aliquots of 1 ml are immediately filtered through Whatman GF/C glassfibre filters and washed with 2×5 ml of the above mentioned buffer. The amounts of radioactivity on the filters are determined by conventional scintillation counting. One group of untreated mice serves as control. One to three mice are injected with 25 μg/kg clonazepam i.p. 30 minutes before $^3$H-FNM to determine the amount of non-specific $^3$H-FNM binding, which should be between 8–15% of total binding. When doses of 100 mg/kg inhibit more than 50% of specific $^3$H-flunitrazepam binding; test substances are administered in doses, which are factors of 3.16 times lower than 100 mg/kg. The $ED_{50}$ for a test substance is defined as that dose which inhibits 50% of specific $^3$H-FNM binding. Specific binding is the amount of binding in controls minus the amount binding in clonazepam-treated mice.

Results. The $ED_{50}$ value is determined from dose response curves. If only one dose of test substance is administered the $ED_{50}$ value is calculated as follows, provided that the inhibition of specific binding is within the range of 25–75%.

$$ED_{50} = \text{(administered dose)} \times \frac{1}{\left(\frac{C_o}{C_x} - 1\right)} \text{ mg/kg}$$

where $C_o$ is specific binding in controls and $C_x$ is specific binding in mice treated with test substance.

Test results obtained by testing some compounds of the invention will appear from the following table I.

salt thereof, may be placed into the form of pharmaceutical compositions and unit dosages thereof, and in such form may be employed as solids, such as tablets or filled capsules, or liquids. such as solutions. suspensions, emulsions. elixirs, or capsules filled with the same, all for oral use, in the form of suppositories for reotal administration; or in the form of sterile injectable solutions for parenteral (including subcutaneous) use. Such pharmaceutical compositions and unit dosage fors thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions,

TABLE 1

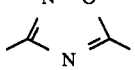

| $R^4$ | X | —A— | $R^3$ | in vivo bind. $ED_{50}$ mg/kg |
|---|---|---|---|---|
| —C≡CSiMe$_3$ | C | —C(=O)—NMe— | 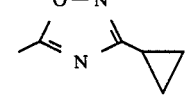 | 3.7 |
| H | N | —NMe—C(=O)— | 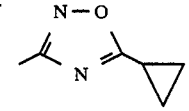 | 0.9 |
| —O—⟨⟩—F | C | —C(=O)—NMe— | 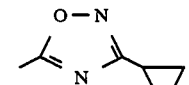 | 2.9 |
| H | C | —NEt—C(=O)— | 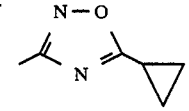 | 1.4 |
| H | N | —NEt—C(=O)— | 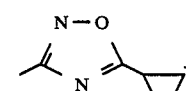 | 0.7 |

The compound of the invention, together with a conventional adjuvant, carrier, or diluent, and if desired in the form of a pharmaceutically-acceptable acid addition alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets. dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.05-100 mg in a pharmaceutically-acceptable carrier per unit dosage.

A typical tablet which may be prepared by conventional tabletting techniques contains:

| | |
|---|---|
| Active compound | 1.0 mg |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the socalled benzodiazepin receptors, which requires such psychopharmaceutioal treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1-200 milligrams daily, 1-100 milligrams daily, and especially 1-30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

A Isatoic anhydride 7.5 g of 2-amino benzoic acid hydrochloride was mixed with i0 ml of diphosgene and the mixture was stirred in 150 ml of dioxane for 40 minutes at reflux. The resulting mixture was cooled and filtered. Yield: 5.7 g of title compound.

In the same manner, from the appropriate aminobenzoic acids, the following compounds were synthesized:
6-chloroisatoic anhydride
6-bromoisatoic anhydride
6-methylisatoic anhydride B. 1,2,3,4-tetrahydro-3-methyl-2,4-dioxo-quinazoline 6 g isatoic anhydride was stirred in 100 ml dry tetrahydrofurane (THF) and methylamine was passed through the mixture for 5 min. The resulting solution was evaporated and the residue was again dissolved in THF (100 ml) and charged with 15 ml 30% phosgene solution in toluene. The mixture was heated to reflux and additional 15 ml phosgene solution was added. After 4 hours reflux the mixture was cooled and evaporated to dryness. The residue was treated with water and the crystals were collected by filtration. The yield was 3.5 g. M.p. 240.4° -240.5° C. In the same manner, from the appropriate substituted isatoic anhydrides, the following compounds were synthesized:
3-methyl-5-chloro-2,4-dioxo-1,2,3,4-tetrahydroquinazoline. M.p. 226°-229° C.
3-methyl-5-bromo-2,4-dioxo-1,2,3,4-tetrahydroquinazoline. M.p. 280° C.
3-methyl-5-methyl-2,4-dioxo-1,2,3,4-tetrahydroquinazoline.

C. 1,2,3,4-tetrahydro-3-ethyl-2,4-dioxo-quinazoline

To a mixture of 12.23 g of ethylamine hydrochloride , 35 ml 4M sodium hydroxide and 175 ml methylene chloride was added 16,3 g isatoic anhydride. This mixture was stirred for 4 hours and the aqueous phase was made basic with 4 M sodium hydroxide. The organic phase was evaporated in vacuo. The residue was dissolved in 300 ml of tetrahydrofuran (THF) and 75 ml phosgene solution (20% in toluene) was added. The resulting mixture was stirred at 80° C. for two hours. The precipitate was filtered off and the mother liquor was evaporated leaving 5.2 g of the title compound. M.p. 189.8°-189.9° C.

D. 1,2,3,4-tetrahydro-1-methyl-2,3-dioxoquinoxaline

A mixture of 12 g of 98% oxalylchloride in 19.5 ml of triethylamine and 50 ml of toluene was added dropwise to a stirred solution of 8.5 g of o-N-methylamino aniline in 80 ml of toluene. The resulting mixture was heated at reflux for one hour. The precipitate was washed wih ether. The residue was stirred with water and filtered to give 1,2,3,4-tetrahydro-1-methyl-2,3-dioxo-quinoxaline.

1,2,3,4-tetrahydro-1-ethyl-2,3-dioxoquinoxaline was prepared in exactly the same manner from o-N-ethylaminoaniline

E. 1,2,3,4-Tetrahydro-3-methyl-2,4-dioxo-5-trimethylsilylethynyl-quinazoline.

To a degassed solution of 5-bromo-3-methyl-2,4-dioxo-1,2,3,4-tetrahydro-quinazoline (1.0g,4.0mmol) in 20 ml of DMF and 20 ml of triethylamine was added trimethylsilylacetylene (1.6ml,12mmol), 50mg of triphenylphosphine, 20mg of palladium(II)acetate, and 1 mg of cuprous(I)iodide. The mixture was stirred under nitrogen, at 70° C.. After 7h additionally 0.4ml of trimethylsilylacetylene was added and hating continued for 4h. Then the mixture was evaporated in vacuo and the residue extracted with 100 ml of dichloromethane and 100 ml of water. The organic layer was washed twice with 100 ml of water dried over anhydrous sodium sulfate, treated with charcoal, filtered through a pad of celite, and evaporated. The residue was triturated with ether/petroleum ether (1:1) and filtered off and dried giving 0.50g (46%) of 1,2,3,4-tetrahydro-3-methyl-2,4-dioxo5-trimethylsilylethynyl-quinazoline.

F. 3-cyclopropyl-5-isocyanomethyl-1,2,4-oxadiazole a. 3-cyclopropyl-5-formylaminomethyl-1,2,4-oxadiazole.

A solution of ethyl formylaminomethyl-carboxylate (150 mmol) and cyclopropyl carboxamide oxime (100 mmol) in 100% EtOH (100 ml) was charged with Na (200 mg) and crushed molecular sieve (4 |) (10 g). The mixture thus obtained was stirred and heated to reflux for 8 hours. The mixture was cooled to room temperature, filtered through filter aid and the filtrate was evaporated in vacuo. The oily residue was partitionated into a CHCl$_3$ phase which was dried with Na$_2$SO$_4$ and evaporated.

3-methyl-5-formylaminomethyl-1,2,4-oxadiazole, 3-ethyl-5-formylaminomethyl-1,2,4-oxadiazole, and 3-methoxymethyl-5-formylaminomethyl-1,2,4-oxadiazole were prepared in exactly the same manner from the appropriate carboxamide oximes.

b. 3-cyclopropyl-5-isocyanomethyl-1,2,4-oxadiazole.

A stirred solution of 3-cyclopropyl-5-formylaminomethyl-1,2,4 1,2,4-oxadiazole (60 mmol) and triethylamine (176 mmol) in CH$_2$Cl$_2$ (100 ml) was charged dropwise with POCl$_3$ (60 mmol) at 0° C. The mixture was then left for 30 minutes with stirring at 0° C., whereafter a solution of Na (60 mmol) in H$_2$O (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 cm$^{-1}$.

3-ethyl-5-isocyanomethyl-1,2,4-oxadiazole was prepared from 3-ethyl-5-formylaminomethyl-1,2,4-oxadiazole in a similar manner. IR: cm$^{-1}$: 2170.

3-methyl-5-isocyanomethyl-1,2,4-oxadiazole was prepared from 3-methyl-5-formylaminomethyl-1,2,4-oxadiazole in a similar manner. IR: cm$^{-1}$: 2170.

3-methoxymethyl-5-isocyanomethyl-1,2,4-oxadiazole was prepared from 3-methoxymethyl-5-formylaminomethyl-1,2,4-oxadiazole in a similar manner. IR: cm$^{-1}$ 2170.

G. 5-cyclopropyl-3-isocyanomethyl-1,2,4-oxadiazol a. Formylaminomethyl-carboxamide oxime.

0.55 mmol of freshly liberated hydroxylamine dissolved in 370 ml methanol was added to 53.6 g (0.638 mmol) N-formylamino-acetonitrile. An ice bath was used to keep the temperature below 20° C. during addition. The solution was allowed to stand at room temperature overnight, whereafter it was evaporated to give the title compound as pale crystals. Decomp. 104°–110° C.

b. 3-formylaminomethyl-5-cyclopropyl-1,2,4-oxadiazole

A mixture of 35 ml ethyl cyclopropylcarboxylate , 20 g formylamino-methylcarboxamide oxime, 1 g sodium and 30 g of crushed molecular sieve (4 Å) was refluxed in 300 ml abs. EtOH for 8 hours whereafter a further 1 g sodium was added The reaction mixture was filtered and the filtrate was evaporated. The dark oily residue was suspended in 300 ml CHCl$_3$, filtered and the filtrate was evaporated to give the title compound as an oil. H-NMR (60 MHz, CDCl$_3$) (ppm): 1.2 (4H, m), 2.8 (1H, m), 4.5 (2H, d, J=6Hz), 7.8 (1H, broad-NH), 8.2 (1H, s).

The following compounds were synthesized from the appropriate ethyl esters in a similar manner:

3-Formylaminomethyl-5-ethyl-1,2,4-oxadiazole. H-NMR(60 MHz, CDCl$_3$) (ppm): 1.4 (3H, t, J=8 Hz), 2.9 (2H, q, J =8Hz) 4.55 (2H, s) ,7.8 (1H, broad-NH), 8.25 (1H, s).

3-Formylaminomethyl-5-methyl-1,2,4-oxadiazole. H-NMR (60 MHz, CDCl$_3$) (ppm); 2.6 (3H, s), 4.6 (2H, d, J=3 Hz), 7.4 (1H, broad-NH), 8.25 (1H, s).

3-Formylaminomethyl-5-methoxymethyl-1,2,4-oxadiazole H-NMR (60 MHz, CDCl3) (ppm): 3.5 (3H, s), 4.7 (4H, s+d, J=6 Hz), 7.8 (1H, broad-NH), 8.25 (H, s).

c. 5-Cyclopropyl-3-isocyanomethyl-1,2,4-oxadiazole A stirred solution of 5-cyclopropyl-3-formylaminomethyl-1,2,4-oxadiazole (60 mmol) and triethylamine (176 mmol) in CH$_2$Cl$_2$(100 ml) was charged dropwise with POCl$_3$ (60 mmol) at 0° C. The mixture was then left for 30 minutes with stirring at 0° C., whereafter a solution of Na (60 mmol) in H$_2$O (50 ml) was added. The mixture was heated to room temperature, evaporated in vacuo. The residue was treated with ether, decanted and the solution was evaporated to give the title compound as an oil. The oil was processed without any further purification. The compound was characterized by its IR absorbtion band at 2160 cm$^{-1}$.

5-Ethyl-3-isocyanomethyl-1,2,4-oxadiazole,
5-methyl-3-isocyanomethyl-1,2,4-oxadiazole, and
5-methoxymethyl-3-isocyanomethyl-1,2,4-oxadiazole were prepared in a similar manner. All compounds were oils and were characterized by their IR stretching band at 2160 cm$^{-1}$.

H. 3-(5-ethyl-1,2,4-oxadiazol-3-yl)-4,5-dihydro-4-methyl-5-oxo-imidazo(1,5-a)quinazoline 3-methyl-1,2,3,4-tetrahydro-2,4-dioxo-quinazoline ( mmol) was dissolved in dry dimethyl formamide DMF (20 ml) and charged with sodium hydride (6 mmol). The resulting solution was cooled under N$_2$ to −20° C., whereafter chlorodiethylphosphate (6 mmol) was added. The reaction mixture was kept under N$_2$with stirring and was allowed to reach room temperature and was then charged with a −30° C. cold solution of 5-ethyl-3-isooyanomethyl-1,2, 4-oxadiazole(6 mmol) and K-t-butylate (6mmol) in dry DMF (15 ml). The resulting mixture was stirred at room temperature for one hour whereafter the reaction mixture was evaporated in vacuo. The residue was partitioned between ethyl acetate and 4M sodium hydroxide. The organic phase was dried and evaporated. Yield 120 mg of title compound. M.p. 199.4°–202.2° C.

In the same manner the following compounds were synthesized:

Ethyl 4,5-dihydro-4-methyl-5-oxo-6-chloro-imidazo(1,5-a)quinazoline-3-carboxylate. M.p. 248-254° C. by reaction between 3-methyl-5-chloro-1,2,3,4-tetrahydro-2,4-dioxo-quinazoline and ethyl isocyanoacetate.

Ethyl 4,5-dihydro-4-ethyl-5-oxo-imidazo(1,5-a)quinazoline-3-carboxylate, by reaction between 3-ethyl-1,2,3,4-tetrahydro-2,4-dioxo-quinazoline and ethyl isocyanoacetate.

Ethyl 4,5-dihydro-5-ethyl-4-oxo-imidazo(1,5-a)quinoxaline-3-carboxylate, by reaction between 1-ethyl-1,2,3,4-tetrahydro-2,3-dioxo-quinoxaline and ethyl isocyanoacetate.

3-(5-cyclopropyl-1,2,4-oxadiazol-3-yl)-4,5-dihydro-4-methyl-5-oxo-6-chloro-imidazo(1,5-a)quinazoline. M.p. 230°–240° C. (decomp.) by reaction between 3-methyl-5-chloro-1,2,3,4-tetrahydro-2,4-dioxo-quinazoline and 5-cyclopropyl-3-isocyanomethyl-1,2,4-oxadiazole.

3-(5-cyclopropyl-1,2,4-oxadiazol-3-yl)-4,5-dihydro-4-methyl-5-oxo-6-bromo-imidazo(1,5-a)quinazoline. M.p. 206,6° C. by reaction between 3-methyl-5-bromo-1,2,3,4-tetrahydro-2,4-dioxo-quinazoline an 5-cyclopropyl-3-isocyanomethyl-1,2,4oxadiazole.

3-(5-methyl-1,2,4-oxadiazol-3-yl)-4,5-dihydro-4-methyl-5-oxo-6-methyl-imidazo(1,5-a)quinazoline. M.p. 237-238° C. by reaction between 3-methyl-5-methyl-1,2,3,4-tetrahydro-2,4-dioxo-quinazoline and 5-methyl-3-isocyanomethyl-1,2,4oxadiazole.

A mixture of 4,5-Dihydro-4-methyl-3-(5-methyl-1,2,4-oxadiazol-3-yl)-5-oxo-6-trimethylsilylethynyl-imidazo(1,5-a)quinazoline, M.p. 214°–217° C., and 6-ethynyl-4,5-dihydro-4-methyl-3-(5-methyl-1,2,4-oxadiazol-3-yl)-5-oxo-imidazo(1,5-a)quinazoline, M.p. 202-206° C.. by reaction between 5-methyl-3-isocyanomethyl-1,2,4-oxadiazole and 1,2,3,4-tetrahydro-3-methyl-2,4-dioxo-5-trimethylsilylethynyl-quinazoline. Column chromatography(silica gel)ethyl acetate) of the crude product yielded 0.08g (12%) of 4,5-dihydro-4-methyl-3-(5-methyl-1,2,4-oxadiazol-3-yl)-5-oxo-imidazo(1,5-a)quinazoline and 0.Olg (1.9%) of 6-ethynyl-4,5-dihydro-4-methyl-3-(5-methyl-1,2,4-oxadiazol-3-yl)-5-oxo-imidazo(1,5-a)quinazoline.

EXAMPLE 2

A. Methoxyacetamide oxime 2.3 g of sodium in 33 ml of dry methanol was mixed with 6.55 g of hydroxylamine hydrochloride in 66 ml of dry methanol. The mixture was filtered and 7.8 g of methoxyacetonitrile was added dropwise to the filtrate. The mixture was left for 48 hours. The mixture was then cooled to 4° C. Filtration and evaporation of the filt rate give 8.7 g of the title compound.

The following compounds were synthesized from the appropriate nitriles in an analogous manner:
Acetamide oxime
Propionamide oxime
Cyclopropyl carboxamide oxime
Isopropyl carboxamide oxime

B. 3-(3-methoxymethyl-1,2,4-oxadiazol-5-yl)-4,5-dihydro-4-ethyl-5-oxo-imidazo(l,5-a)quinazoline 50 mg of sodium hydride was dissolved in 50 ml of dry ethanol containing 3 g of a molecular sieve (4 Å) and 0.5 g of methoxyacetamide oxime was added to this mixture and thereupon 0.5 g of ethyl 4,5-dihydro-4-ethyl-5-oxo-imidazo(1,5-a)quinoxaline-3-carboxylate. The resulting mixture was refluxed for hours. The product was isolated by filtration, reduction of the volume of the reaction mixture in vacuo followed by addition of icewater and filtration.

Yield: 220mg of the title compound M.p. 176.0–176.3° C.

C. 3-(3-cyclopropyl-1,2,4-oxadiazol-5-yl)-4,5-dihydro-4-methyl-5-oxo-6-chloro-imidazo(1,5-a)quinazoline and 3-(3-cyclopropyl-1,2,4-oxadiazol-5-yl)-4,5-dihydro-4-methyl-5-oxo-6-ethoxy-imidazo(1,5-a)quinazoline 50 mg of sodium was dissolved in 20 ml of dry ethanol containing 3 g of molecular sieves (4 Å) and 0.5 g of cyclopropylcarboxamide oxime was added to this mixture and thereupon 0.2 g of ethyl 4,5-dihydro-4-methyl-5-oxo-6-chloro-imidazo(1,5-a)quinoxaline-3-carboxylate. The resulting mixture was refluxed for 2 hours. The product was isolated by filtration, reduction of the volume of the reaction mixture in vacuo followed by addition of icewater and filtration. T.L.C. showed content of two compounds, which were isolated by chromatography on silica gel with ethyl acetate.

Yield: 5.7mg of 6-chloro compound M.p. 200°–205° C. 5.Omg of 6-ethoxy compound M.p. 238°–240° C.

EXAMPLE 3.

6-cyano-3-(5-cyclopropyl-1,2,4-oxadiazol-3-yl)-4,5-dihydro-4-methyl-5-oxo-imidazo(1,5-a)quinazoline.

To 140 mg 6-bromo-3-(5-cyclopropyl-1,2,4-oxadiazol-3-yl)-4,5-dihydro-4-methyl-5-oxo-imidazo(1,5-a)quinazoline in 5 ml dimethyl formamide (DMF) 40 mg cuprous cyanide was added. Thereafter further 5 ml DMF was added and the resulting mixture was heated to 130° 150° C. for 60 minutes with stirring. To this mixture 110 mg sodium cyanide in 5 ml water was added and thereafter further 30 ml water. The resulting mixture was extracted with 30 ml ethyl acetate and thereafter four times with 20 ml ethyl acetate. The combined organic phase was washed with water and dried with calcium chloride. Evaporation in vacuo gave 24 mg of the title compound. M.p. 115°–125° C.

EXAMPLE 4

3-(5-cyclopropyl-1,2,4-oxadiazol-3-yl)-4-methyl-5-oxo-6-benzyloxy-4,5-dihydro-imidazo(1,5-a)quinazoline A mixture of (3-(5-cyclopropyl-1,2,4-oxadiazol-3-yl)-4-methyl5-oxo-6-chloro-4,5-dihydro-imidazo(1,5-a)quinazoline (0.4 g, 1.2 mmol), benzyl alcohol (0.32 g, 3 mmol), and sodium hydride (55% dispension in oil, 0.13 g, 3 mmol) in 20 ml of dry DMF (dimethylformamide) was stirred for 5 h at 110° C., then cooled to room temperature and was thereafter poured into 30 ml of water and 5 ml of ether. The mixture was then stirred for 1 h at 0° C. and the precipitate was filtered off, rinsed with water and dried giving 0.26 g (53%) of 3-(5-cyclopropyl-1.2.4-oxadiazol-3-yl)-4-methyl-5-oxo- 6-benzyloxy-4,5-dihydro-imidazo (1,5-a)quinazoline, M.p. 221°-224° C.

EXAMPLE 5

3-(5-cyclopropyl-1,2,4-oxadiazol-3-yl)-4-methyl-5-oxo-6-3-chlorophenoxy)-4,5-dihydro-imidazo(1,5-a)quinazoline A mixture of 3-(5-cyclopropyl-1,2,4-oxadiazol-3-yl)-4-methyl-5-oxo-6-chloro-4,5-dihydro-imidazo(1,5-a)quinazoline (0.4 g, 1.2 mmol), 3-chlorophenol (0.4 g, 3 mmol), and sodium hydride (55% dispension in oil, 0.14 g, 3 mmol) in 20 ml of dry dimethylformamide was stirred for 8 h at 110° C., cooled to room temperature and poured into 30 ml of water and 5 ml of ether. The mixture was then stirred for 30 min. at 0° C. and the precipitate was filtered off, rinsed with water and dried giving 0.28 g (57%) of 3-(5-cyclopropyl-1,2,4- oxadiazol-3-yl)-4-methyl-5-oxo-6-(3-chlorophenoxy)-4,5-dihydroimidazo(1, 5-a) quinazoline, M.p. 201°-203° C.

The following compounds were prepared in exactly the same way from the appropriate 6-chloro imidazoquinazoline. phenol and 4-fluorophenol:

3-(5-cyclopropyl-1,2,4-Oxadiazol-3-yl)-4-methyl-5-oxo-6-phenoxy-4,5-dihydro-imidazo(1,5-a)quinazoline, M.p. 209.3-210° C.

3-(5-cyclopropyl-1,2,4-oxadiazol-3-yl)-4-methyl-5-oxo-6-(4-fluorophenoxy)-4,5-dihydro-imidazo(1,5-a)quinazoline, M.p. 229.7°-229.8° C.

3-(3-cyclopropyl-1,2,4-oxadiazol-5-yl)-4-methyl-5-oxo-6(4-fluorophenoxy)-4,5-dihydro-imidazo(1,5-a)quinazoline, M.p. 270°-271° C.

EXAMPLE 6

3-(5-cyclopropyl-1,2,4(oxadiazol-3-yl)-4-methyl-5-oxo-6-1-piperidyl)-4,5-dihydro-imidazo(1.5-a)quinazoline 3-(5-cyclopropyl-1,2,4-oxadiazol-3-yl)-4-methyl-5-oxo-6-chloro-4,5-dihydro-imidazo(1,5-a)quinazoline (0.28 g, 0.8 mmol) was heated to 110° C. for 2 ¼ h in a mixture of 20 ml of dimethylformamide and 1 ml of piperidine. The reaction mixture was then evaporated in vacuo and the residue triturated with 5 ml of water, filtered off and dried to give 0.26 g (81%) 3- (5-cyclopropyl-1,2,4-oxadiazol-3-yl)-4-methyl -5-oxo- 6-(1-piperidyl)-4,5-dihydro-imidazo(1,5-a)quinazoline, M.p. 185°-192° C..

EXAMPLE 7

3-(5-cyclopropyl-1,2,4-oxadiazol-3-yl)-4-methyl-5-oxo-6-dimethylamino-4,5-dihydro-imidazo(1,5-a)quinazoline Gaseous dimethylamine was passed through a stirred solution of 3-(5-cyclopropyl-1,2,4-oxadiazol-3-yl)-4-methyl-5-oxo-6-chloro-4,5-dihydro-imidazo(1,5-a)quinazoline (0.4 g, 1.2 mmol) in 25 ml of dry dimethylformamide at 110° C. for 2 h. The reaction mixture was evaporated in vacuo and the residue was triturated with 20 ml of water, filtered off and dried to give 0.35 g (86%) of 3-(5-cyclopropyl-1,2,4-oxadiazol-3-yl)-4-methyl-5-oxo-6-dimethylamino-4,5-dihydro-imidazo(1,5-a)quinazoline, M.p. 170°-171° C.

3-(3-cyclopropyl-1,2,4-oxadiazol-5-yl)-4-methyl-5-oxo-6-dimethylamino-4,5-dihydro-imidazo(1,5-a)quinazoline M.p. 214° C. was prepared in exactly the same manner from 3-(3-cyclopropyl-1,2,4-oxadiazol-5-yl)-4-methyl-5-oxo-6-chloro-4,5- dihydro-imidazo(1,5-a)quinazoline.

EXAMPLE 8

3-(5-cyclopropyl-1,2,4-oxadiazol-3-yl)-4-methyl-5-oxo-6-(O-(-)-menthyl)-4,5-dihydro-imidazo(1,5-a)quinazoline A mixture of 3-(5-cyclopropyl-1,2,4-oxadiazol-3-yl)-4-methyl-5-oxo-6-chloro-4,5-dihydro-imidazo(1,5-a)quinazoline (0.4 g, 1,2 mmol), (1R,2S,5R)-2-isopropyl-5-methyl-cyclohexanol (0.47 g, 3 mmol), and sodium hydride (55% dispersion in oil, 0.12 g, 3 mmol) in 20 ml of dry DMF was stirred for 4h at 110° C. The reaction mixture was then cooled to room temperature acidified by addition of 1 ml of glacial acetic and evaporated in vacuo. The residue was purified by column chromatography on silica gel using a 9:1 mixture of ethyl acetate and methanol as eluent. Yield 0.18 g (33%) of 3-(5-cyclopropyl-1,2,4,-oxadiazol-3-yl)-4-methyl-5-oxo-6 -(O-(-)-menthyl)-4,5-dihydro-imidazo(1,5-a)quinazoline, M.p.139°-144° C..

EXAMPLE 9 a. 3-amino-2(N-methylamino)-pyridine, hydrochloride 2-chloro-3-nitro-pyridine (16g) was dissolved in dry tetrahydrofuran (200ml). The solution was exposed to gaseous methylamine untill the reaction to N-methylamino-3-nitropyridine was completed. The mixture was filtered and the filtrate was evaporated. The yellow residue was dissolved in 96% EtOH (250ml) and was charged with 5% Pd/C (1 g) and hydrogenated under standard conditions. After completion of the hydrogenation an aqueous solution of hydrochloric acid was added (5Oml,4N), the Pd catalyst was filtered of and the filtrate was evaporated to give the title compound as an oil.

In a similar manner 3-amino-2(N-ethyl amino) pyridine hydrochloride was prepared from 2-chloro-3-nitropyridine and ethylamine.

b. 1,2,3,4-tetrahydro-4-methyl-2,3-dioxo-pyrido(2,3-b)pyrazine 3-amino-2-(N-methylamino)-pyridine (0.1 mol)and oxalic acid dihydrate (0,12mol) was dissloved in 4N HCI (400 ml). The solution was refluxed for 8 hours and then cooled to room temperature whereby the title compound precipitated as crystals. The crystals were separated by filtration and then washed with water. m.p. 271°-272° C.

In a similar manner 4-ethyl-1,2,3,4-tetrahydro-2,3-dioxopyrido(2,3-b)pyrazine was prepared from 3-amino-2(Nethylamino)pyridine and oxalic acid. M.p. 238°-239° C.

c. 1,2-dihydro-2-oxo-4-phenyl-quinoline

A mixture of o-amino benzophenone (10 g) and acetic acid anhydride (10 ml) in tetrahydrofuran (150 ml) was refluxed for 8 hours. The mixture was thereafter evaporated and the residue was partitioned between sat NaHC03, (20ml) and diethylether (15Oml). The organic phase was dried and evaporated to give an yellow oil which was redissolved in dimethyl formamide (150ml). To this solution was added NaH (5g) and the mixture was stirred at 110° C. for 1½ hour, whereafter it was cooled to room temperature, and poured into water (300ml). This treatment afforded a precipitate of the title compound as pale crystals, which were collected by filtration. The crystals were washed with water and dried. M.p. 244°–247° C..

d. Ethyl 4,5-dihydro-5-methyl-4-oxo-imidazo(1,5-a)pyrido(2,3-e)pyrazine-3-carboxylate To a stirred solution of 1,2,3,4-tetrahydro-4-methyl-2,3-dioxo-pyrido(2,3-b)-pyrazine (5g) in 50 ml of dry dimethyl formamide (DMF) was added potassium-t-butylate (4 g). The mixture was allowed to stir at room temperature for 15 min whereafter it was cooled to −25° C. and charged with diethyl chlorophosphate (5ml). Stirring continued at 0° C. for 15 min, then it was cooled to −20° C. whereafter a preformed −30° C. cold solution of ethyl isocyanoacetate (3.9ml) and pottasium-t-butylate (4 g) in 30ml of dry DMF was added. The resulting solution was allowed to obtain room temperature before acetic acid was added (1,5 ml). The DMF was removed by evaporation in vacuo, whereafter the residue was treated with water to give the crude title compound as pale crystals. Recryst in 96% ETOH M.p. 233°–234° C.

The following compounds were prepared in a similar manner:

4,5-dihydro-5-methyl-3-(5-methyl-1,2,4- oxadiazol-3-yl)-4-oxoimdazo (1,5-a)pyrido(2,3-e)pyrazine starting from 1,2,3, 4-tetrahydro-4-methyl-2,3-dioxo-pyrido(2,3-b) pyrazine and 3-isocyanomethyl-5-methyl-1,2,4-oxadiazole. M.p. 260.1°–260.2° C.

Ethyl 5-et hyl-4,5-dihydro-4-oxo-imidazo(1,5-a)pyrido(2,3-e)-pyrazine-3-carboxylate was prepared from 4-ethyl-1,2,3,4-tetrahydro-2,3-dioxo-pyrido(2,3-e)pyrazine and ethyl isocyanoacetate. M.p. 215.5°–216.8° C.

3-(5-cyclopropYl-1,2,4-oxadiazol-3-yl)-5-ethyl-4,5-dihydro4-oxo-imidazo(1,5-a)pyrido(2,3-e)pyrazine was prepared from 4-ethyl-1,2,3,4-tetrahydro-2,3-dioxo-pyrido(2,3-e)pyrazine and 3-isocyanomethyl-5-cyclopropyl-1,2,4-oxadiazole. M.p. 254.3°–255.4° C.

Ethyl 5-phenyl-imidazo(1,5-a)quinoline-3-carboxylate was prepared from 1 2-dihydro-2-oxo-4-phenyl-quinoline and ethyl isocyanoacetate. M.p. 176°–185° C.

EXAMPLE 10

3-(3-cyclopropyl-1,2,4-oxadiazol-5-yl)-5-phenyl-imidazo(1,5-a)quinoline

Sodium (70mg) was dissolved in 60ml absolute dry alcohol. To this solution was added ethyl 5-phenyl-imidazo(1,5-a)quinoline-3-carboxylate (200mg),cyclopropyl carboxamidoxime (300mg) and crushed molecular sieves (5g,4 Å), and the mixture was refluxed for 24 hours. The mixture was then cooled and filtered through filter aid, whereafter the filtrate was concentrated to 10ml in vacuo. Addition of water (50 ml) afforded precipitation of the title compound as pale crystals. The crystals were collected and washed with water. M.p. 268°–269° C.

In a similar manner with the exception of varying reflux time, the following compounds were prepared:

3-(3-cyclopropyl-1,2,4-oxadiazol-5-yl)-4,5-dihydro-5-methyl-4-oxo-imidazo(1,5-a)pyrido(2,3-e)pyrazine was prepared from ethyl 4,5-dihydro-5-methyl-4-oxo-midazo(1,5-a)pyrido(2,3-e)pyrazine-3-carboxylate and cyclopropyl carboxamidaxime. Reflux time 1 hour. M.p. 266.1°–268.6° C.

5-ethyl-4,5-dihydro-3-(3-methyl-1,2,4-oxadiazol-5-yl)-4-oxo- imidazo(1,5-a)pyrido(2,3-e)pyrazine was prepared from ethyl 5-ethyl-4,5-dihydro-4-oxo-imidazo(1,5-a)pyrido(2,3-e)pyrazine-3-carboxylate and methyl carboxamidoxime. Reflux time 1 hour. M.p. 251°–252° C.

3-(3-cyclopropyl-1,2,4-oxadiazol-5-yl)-5-ethyl-4,5-dihydro-4-oxo-imidazo(1,5-a)pyrido(2,3-e)pyrazine was prepared from ethyl 5-ethyl-4,5-dihydro-4-oxo-imidazo(1,5-a)pyrido(2,3-e)pyrazine-3-carboxylate and cyclopropyl-carboxamidoxime. Reflux time 1/2 hour. M.p. 262°–263° C.

5-ethyl-3-(3-ethyl-1,2,4-oxadiazol-5-yl)-4,5-dihydro-4- oxo-imidazo(1,5-a)pyrido(2,3-e)pyrazine was prepared from ethyl 5-ethyl-4,5-dihydro-4-oxo-imidazo(1,5-a)pyrido(2,3-e)pyrazine-3-carboxylate. M.p. 220.6–220.7

EXAMPLE 11

5-ethyl-4,5-dihydro-4-oxo-imidazo(1,5-a)quinoxaline-3-N,N-dimethyl-carboxamide.

A mixture of a sodium hydroxyde solution (4,5m1,4N), water (15ml), 96% ethanol (5ml) and ethyl 5-ethyl-4,5-dihydro-4-oxo-imidazo(1,5-a)quinoxaline-3-carboxylate (2g) was refluxed on steam bath for 15 min. The solution was cooled and 5 ml 4N hydrochloric acid was added. The ethanol was evaporated and the precipitated crystals was filtered off and dried, whereafter the crystals was suspended in tetrahydrofuran (20ml) and N,N-carbonyl diimidazol (1,6g) was added. The mixture was refluxed for 6 hours whereafter a stream of gaseous dimethylamine was led through the reaction mixture for 10 min. Then it was cooled to room temperature and filtered. The filtrate was evaporated to give the title compound as white crystals. M.p. 130.4°–132.2° C.

EXAMPLE 12 a.

6-Chloro-4,5-dihydro-4-methyl-5-oxo-imidazo(1,5-a)quinazoline-3-carboxylic acid.

Ethyl 6-chloro-4,5-dihydro-4-methyl-5-oxo-imidazo(1,5-a)quinazoline-3-carboxylate (2.27g,7.4mmol) in a mixture of 50ml of ethanol, 25ml of water and 4.6ml of 4M aquous sodium hydroxide was refluxed for 1h. Then the mixture was cooled to 0° C. and neutralized by addition of 4.6ml of 4M hydrochloric acid. The precipitate was filtered off, rinsed with water and dried to give 2.1g (100%) of 6-chloro-4,5-dihydro-4-methyl-5-oxo-imidazo(1.5-a)quinazoline- 3-carboxylic acid.

b.

1-((6-Chloro-4,5-dihydro-4-methyl-5-oxo-imidazo(1,5-a)quinazoline-3-yl)carbonyl)-imidazole.

To a stirred suspension of 6-chloro-4,5-dihydro-4-methyl-5-oxo-imidazo(1,5-a)quinazoline-3-carboxylic acid (2.1g,7.4mmol) in 50ml of tetrahydrofuran was gradually added 1,1'-carbonyldimidazole (1.74 g, 10.7 mmol) at room temperature, whereafter the mixture was refluxed for 7h. The reaction mixture was evaporated in vacuo and the residue triturated with 30ml of water. The precipitate was filtered off, rinsed with water and dried giving 1.56 g (64%) of 1-((6-Chloro-4,5-dihydro-4-methyl-5-oxo-imidazo(1,5-a)quinazoline-3-yl)carbonyl)-imidazole. M.p. 242°–243° C.

c.

6-chloro-4,5-dihydro-4-methyl-5-oxo-imidazo(1,5-a)quinazoline-3-N,N-dimethylcarboxamide. Gaseous dimethylamine was passed through a stirred suspension of 1-((6-chloro-4,5-dihydro-4-methyl-5-oxo-imidazo(1,5-a)-quinazoline-3-yl)carbonyl)-imidazole (0.70 g, 2.1mmol) in 50 ml of refluxing tetrahydrofuran for 30h. The mixture was evaporated in vacuo and the residue triturated with 20ml of water. The precipitate was filtered off rinsed with water and dried. The crude product (1 g) was purified by column chromatography on silica gel using a oil mixture of ethylacetate and methanol as eluent. Yield 0.09 g (14%) of 6-chloro4,5-dihydro-4-methyl-5-oxo-imidazo(1,5-a)quinazoline-3-N,N-dimethylcarboxamide, M.p. >300° C.

We claim:

1. A heterocyclic compound having the formula I

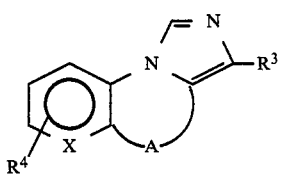

(I)

wherein $R^3$ is $CO_2R'$ or $CONR'R''$, wherein $R'$ and $R''$ independently are $C_{1-6}$-alkyl;

—A— is —C(=O)—NR'''—, NR'''—C(=O)—, or

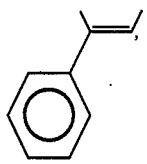

wherein $R''''$ is $C_{1-6}$-alkyl;

X is C or N; and $R^4$ is hydrogen or halogen; provided, however, that A is not —C(=O)—NR''' or —NR'''—C(=O)— when $R^3$ is $CO_2R'$ and X is C and further provided that A is not —NR'''—C(=O)—when $R^3$ is CONR'R''' and X is C.

2. A compound of claim 1 which is ethyl 4,5-dihydro-5-methyl-4-oxo-imidazo(1,5-a)pyrido(2,3-e)pyrazine-3-carboxylate.

3. A compound of claim 1 which is ethyl 5-ethyl-4,5-dihydro-4-oxo-imidazo(1,5-a)pyrido(2,3-e)pyrazine-3-carboxylate.

4. A compound of claim 1 which is ethyl 5-phenyl-imidazo (1,5-a)quinoline-3-carboxylate.

5. A compound of claim 1 which is 6-chloro-4,5-dihydro-4-methyl-5-oxo-imiazo(1,5-a)quinazoline-3-N,N-dimethylcarboxamide.

6. A pharmaceutical composition suitable for use in the treatment of a central nervous system aliment associated with the benezodiazepine receptors comprising an amount of a compound of a compound of claim 1 which is effective for the alleviation of such disorder together ith a pharmaceutically-acceptable carrier or diluent.

7. A pharmaceutical composition according to claim 6 wherein the compound is in the form of an oral dosage unit containing 1–100 mg of the active compound.

8. A method of treating a central nervous system ailment associated with the benezodiazepine receptors in a subject in need of such treatment comprising the step of administering to said subject an amount of a compound of claim 1 which is effective for the alleviation of such ailment.

9. A method of claim 8 wherein said compound is administered in the form of a pharmaceutical composition thereof, in which it is present together with a pharmaceutically-acceptable carrier or diluent.

* * * * *

UNITED STATES PATENT AND TRADEMARK OFFICE
CERTIFICATE OF CORRECTION

PATENT NO. : 4,873,244

DATED : October 10, 1989

INVENTOR(S) : Frank Wätjen and Holger C. Hansen

It is certified that error appears in the above-identified patent and that said Letters Patent is hereby corrected as shown below:

Col. 18, line 31; "benezodiazepine" should read
-- benzodiazepine --

Col. 18, line 40; "benezodiazepine" should read
-- benzodiazepine --

Signed and Sealed this

Fifth Day of June, 1990

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO.  : 4,873,244                                    Page 1 of 4
DATED       : Oct. 10, 1989
INVENTOR(S) : Frank Wätjen, Holger C. Hansen It is certified that error appears in the above-identified patent and that said Letters Patent is hereby corrected as shown below:

Title Page, column 1, Item [75] and under "United States Patent [19]", "Wäjen" should read -- Wätjen -- (both occurrences) - See Declaration Title Page, column 2, Abstract, first formula;

reads                                    should read

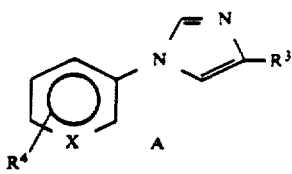 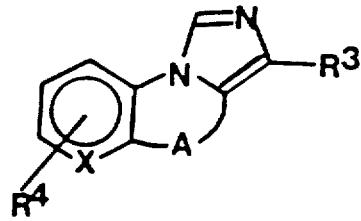

Title Page, column 2, Abstract, second formula;

reads                                    should read

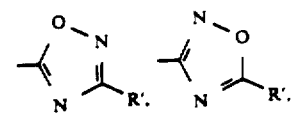 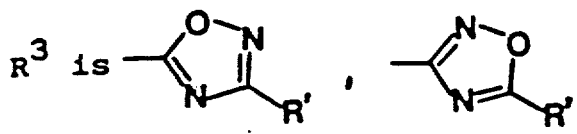

Column 1, line 63; "trimethyl-$C_{1-6}$-alkynl" should read -- trimethylsilyl-$C_{1-6}$-alkynyl --.

Column 2, line 34 "above with" should read -- above, with --.

Column 4, line 8 "(NR'R'') R' should read -- (NR'R'') wherein R' --.

UNITED STATES PATENT AND TRADEMARK OFFICE
CERTIFICATE OF CORRECTION

PATENT NO. : 4,873,244

DATED : Oct. 10, 1989

INVENTOR(S) : Frank Wätjen, Holger C. Hansen

It is certified that error appears in the above-identified patent and that said Letters Patent is hereby corrected as shown below:

Column 6, line 6; "reotal" should read -- rectal --.

Column 6, line 9; "fors" should read -- forms --.

Column 8, line 11; "i0" should read -- 10 --.

Column 8, line 47, "16,3" should read -- 16.3 --.

Column 9, line 12; "hating" should read -- heating --.

Column 9, line 16; "water dried" should read -- water, dried --.

Column 9, line 21, "dioxo5-" should read -- dioxo-5- --.

Column 9, line 29 "sieve (4/)" should read -- (4Å) --.

Column 9, line 48; "Na (60 mmol)" should read -- $Na_2CO_3$ (60 mmol) --.

Column 10, line 12; "formyIamino-methyIcarboxamide" should read -- formylamino-methylcarboxamide --

Column 10, line 15; "added The" should read -- added. The --

Column 10, Line 31; "CDC13)" should read -- $CDCl_3$) --.

Column 10, Line 40; "Na (60" should read -- $Na_2CO_3$(60 --.

Column 10, Line 41/42; "temperature, evaporated" should read --temperature, whereafter the organic phase was separated, dried and evaporated --.

Column 10, line 57/58; "(mmol)" should read -- (5 mmol) --.

Column 10, line 65; "isooyanomethyl" should read --isocyanomethyl --.

Column 11, line 8; "(1,5-a)quinazoline-" should read -- (1,5-a)-quinazoline- --.

UNITED STATES PATENT AND TRADEMARK OFFICE
CERTIFICATE OF CORRECTION

PATENT NO. : 4,873,244
DATED : Oct. 10, 1989
INVENTOR(S) : Frank Wätjen, Holger C. Hansen It is certified that error appears in the above-identified patent and that said Letters Patent is hereby corrected as shown below:

Column 11, line 30; "an 5" should read -- and 5 --.
Column 11, line 31; "-1,2,4oxadiazole." should read
-- -1,2,4-oxadiazole. --
Column 11, line 45/46; "(silica gel)ethyl acetate)" should read
-- (silica gel/ethyl acetate) --.
Column 11, line 48; "0.01g" should read -- 0.01g --.
Column 11, line 61; "filt rate" should read -- filtrate --.
Column 12, line 10; "for hours." should read -- for 2 hours. --.
Column 12, line 68; "-1.2.4-" should read -- 1,2,4- --.
Column 13, line 35/36 "(5-cyclopropyl-1,2,4(oxadiazol - 3-yl)"
should read -- (5-cyclopropyl-1,2,4-oxadiazol-3-yl) --.
Column 13, line 36; "-6-1-" should read -- -6-(1- --.
Column 13, line 37; "(1.5-a)" should read -- (1,5-a) --.
Column 13, line 40; "2¼ h" should read -- 2½ h --.
Column 14, line 26; "untill" should read -- until --.
Column 14, line 33; "of" should read -- off --.
Column 14, line 46; "HCI" should read -- HCl --.
Column 14, line 61; "NaHC03," should read -- NaHCO$_3$, --.
Column 15, line 30; "5-et   hyl-" should read -- 5-ethyl- --.
Column 15, line 35; "3-(5-cyclopropYl-" should read
-- 3-(5-cyclopropyl- --.

UNITED STATES PATENT AND TRADEMARK OFFICE
CERTIFICATE OF CORRECTION

PATENT NO. : 4,873,244

DATED : Oct. 10, 1989

INVENTOR(S) : Frank Wätjen, Holger C. Hansen

It is certified that error appears in the above—identified patent and that said Letters Patent is hereby corrected as shown below:

Column 15, line 36; "dihydro4-oxo-imidazo" should read
-- dihydro-4-oxo-imidazo --

Column 15, line 41; "1 2-" should read -- 1,2- --.

Column 16, line 15; "220.6-220.7" should read
-- 220.6-220.7°C. --.

Column 16, line 27; "crystals was filtered" should read
-- crystals were filtered -- .

Column 16, line 28; "crystals was suspended" should read
-- crystals were suspended --.

Column 16, line 68; "-imidazoIe." should read -- -imidazole. --.

Column 17, line 25; "6-chloro4," should read -- 6-chloro-4, --.

Column 18, line 32; "of a compound of a compound" should read
-- of a compound --.

Signed and Sealed this

Fifth Day of November, 1991

Attest:

HARRY F. MANBECK, JR.

Attesting Officer

Commissioner of Patents and Trademarks